United States Patent
Gallou et al.

(10) Patent No.: US 9,840,534 B2
(45) Date of Patent: Dec. 12, 2017

(54) PROCESS FOR THE MANUFACTURE OF CYCLIC UNDECAPEPTIDES

(71) Applicants: Fabrice Gallou, Basel (CH); Bernard Riss, Huningue (FR)

(72) Inventors: Fabrice Gallou, Basel (CH); Bernard Riss, Huningue (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/198,152

(22) Filed: Jun. 30, 2016

(65) Prior Publication Data

US 2016/0304554 A1    Oct. 20, 2016

Related U.S. Application Data (63) Continuation of application No. 14/399,261, filed as application No. PCT/EP2013/059672 on May 8, 2013, now abandoned.

(60) Provisional application No. 61/644,616, filed on May 9, 2012.

(51) Int. Cl.
| | | |
|---|---|---|
| A61K 38/00 | (2006.01) |
| C07K 1/12 | (2006.01) |
| C07K 7/64 | (2006.01) |
| C07K 1/107 | (2006.01) |
| C07K 7/06 | (2006.01) |

(52) U.S. Cl.
CPC .............. *C07K 1/12* (2013.01); *C07K 1/107* (2013.01); *C07K 7/06* (2013.01); *C07K 7/645* (2013.01); *A61K 38/00* (2013.01)

(58) Field of Classification Search
None
See application file for complete search history.

(56) References Cited

U.S. PATENT DOCUMENTS

| | | |
|---|---|---|
| 2004/0220091 A1 | 11/2004 | Adam et al. |
| 2014/0005100 A1 | 1/2014 | Su et al. |

FOREIGN PATENT DOCUMENTS

| | | |
|---|---|---|
| JP | A-2011-506973 A | 6/2009 |
| WO | 0001715 A1 | 1/2000 |
| WO | 0046239 A1 | 8/2000 |
| WO | 2006038088 A1 | 4/2006 |
| WO | 2010088573 A1 | 8/2010 |

OTHER PUBLICATIONS

Balakrishnan, "Investigations into the microbial production of cyclosporine A", Doctoral dissertation, 1997, Cochin University of Science and Technology, retrieved from: http://dyuthi.cusat.ac.in/xmlui/bitstream/handle/purl/2714/Dyuthi-T0761.pdf?sequence=1.

*Primary Examiner* — Thomas S Heard
(74) *Attorney, Agent, or Firm* — David R. Kurlandsky (57) ABSTRACT

The present invention relates to processes and intermediates useful for the manufacture of cyclic undecapeptides, such as Alisporivir.

2 Claims, 2 Drawing Sheets

FIG. 1 Compound 3

FIG. 2 Compound 4

PROCESS FOR THE MANUFACTURE OF CYCLIC UNDECAPEPTIDES

FIELD OF THE INVENTION

The invention relates to novel process(es), novel process step(s) and novel intermediate(s) useful for the opening of Cyclosporin derivatives and subsequently for the preparation of cyclic polypeptides, more specifically, cyclic undecapeptides, such as alisporivir (also known as DEB025, Debio025, or Debio).

BACKGROUND OF THE INVENTION

The present invention relates to processes for the preparation of cyclic polypeptides, such as, for example, cyclic undecapeptides, such as alisporivir.

Alisporivir is a cyclophilin (Cyp) inhibitor used for the treatment of hepatitis C virus (HCV) infection or HCV induced disorders as described in WO 2006/038088. Furthermore, WO2009/042892 describes methods for the use of alisporivir in the treatment of multiple sclerosis; WO2009/098577 describes methods for the use of alisporivir in the treatment of muscular dystrophy; WO2008/084368 describes methods for the use of alisporivir in the treatment of Ullrich congenital muscular dystrophy.

Alisporivir and a synthesis thereof are described in WO 00/01715. Alisporivir has been attributed the CAS Registry Number 254435-95-5.

Processes for the preparation of Alisporivir on laboratory scale are described by J. F. Guichoux in "De nouveaux analogues de Cycloposrine A comme agent anti-HIV-1" PhD thesis, Faculte des Sciences de L'Universite de Lausanne, 2002, in WO2006/038088, and in WO2008/084368.

Cyclic undecapeptides, as represented below, are cyclic polypeptides of Formula (Ia), wherein n=2.

Alisporivir (Formula I) is a cyclic undecapeptide of Formula (Ib) wherein n=2, aa1 is D-MeAla and aa2 is EtVal.

(Formula Ia)

CYCLIC POLYPEPTIDES
A = Alkyl substituent
$aa_n$ = amino acids (Formula Ib)

CYCLIC UNDECAPEPTIDES
A = Alkyl substituent
$aa_n$ = amino acid (Formula I)

ALISPORIVIR
n = 2, $aa_1$ = D—MeAla, $aa_2$ = EtVal

Generic Formula:
Cyclo-(AXX1-AXX2-AXX3-AXX4-AXX5-AXX6-AXX-7-AXX8-AXX9-AXX10-AXX11), should cover examples from case WO2010/052559 A1 as fragmentation made at key Sar fragment
AXX1=MeBmt, Bmt, MeLeu, Desoxy-MeBmt, Methylaminooctanoic acid
AXXn 2=Abu, Ala, Thr, Val, Nva
AXX3=Sar
AXX4=MeLeu, Val
AXX5=Val, Nva
AXX6=MeLeu, Leu
AXX7=Ala, Abu
AXX8=D-Ala
AXX9=MeLeu, Leu
AXX10=MeLeu, Leu
AXX11=MeVal, Val, D-MeVal
And all other combinations covered in WO 2010/052559 A1

Over the last several years, cyclosporin A (CyA) has been used as a raw material for a variety of synthetic cyclic undecapeptides which are useful for the treatment of inflammatory or viral diseases. Cyclic undecapeptides may be obtained by strain selection, however obtaining most unnatural derivatives requires a chemical transformation which relies on opening of the cyclic polypeptide, for example, of Formula (Ia) or of Formula (Ib) and subsequent amino acid replacement.

Traditionally, cyclic polypeptide, for example of Formula (Ia) are opened in a highly selective process and an amino acid residue is removed via the Edman degradation to access the opened cyclic polypeptide as a key intermediate (Wenger, R. M. In Peptides 1996; Ramage, R.; Epton, R., Eds.; The European Peptides Society, 1996; pp. 173; Wenger, R. M. et al. *Tetrahedron Letters* 2000, 41, 7193.). Numerous scientists and companies have used this reliable and selective strategy wherein pure cyclosporin A and purification by column chromatography have been used to obtain cyclic undecapeptides.

Furthermore, purification of products, such as opened cyclosporin A, involve several steps of purification by liquid chromatography on silica. Beside the moderate overall obtained yield, the major drawback of this purification scheme is the very high costs for the chromatography steps. Large-scale purification processes of such products derived from cyclosporin A or its structural analogues described in the literature generally involve a chromatographic purification or at least a pre-purification by adsorption chromatography. Such pre-purification may be followed, for instance, by extraction, counterflow extraction, and/or supercritical fluid extraction.

However, none of these techniques appear to be fully satisfactory for obtaining the key opened intermediates with the desired quality requirements, with an acceptable overall yield, and at an acceptable cost for an industrial scale production, as costly precursors of high quality were required.

We identified that dimethoxycarbenium ions (described in Novartis patent application EP 0 908 461 A1 for the methylation of Cephalosporine derivatives), do the same chemistry as oxonium ions (trimethyl or triethyloxonium Meerwein salts) in the opening of the macrocyclic polypeptide. The new conditions can advantageously be prepared in situ, thus avoiding the handling of hazardous and hygroscopic substance, can proceed in a variety of solvents such as for example toluene, xylene, anisole, by-passing the need for using the undesirable chlorinated solvents such as dichloromethane or dichloroethane, and avoid the use of oxonium Meerwein salts originating from the genotoxic epichlorhydrin. Either the dedicated carbenium tetrafluoroborate salt or the in situ generated reactive species made by the reaction of boron trifluoride and an orthoester derivative, preferably trimethyl orthoformate, will result in the desired opened polypeptides such as compound 3 below.

We identified an improved process which maintains the advantage of a highly selective Edman degradation strategy while taking full advantage of newly identified crystalline intermediates.

The following disclosure presents newly isolated and crystalline intermediates derived from the opening of cyclosporin A cyclosporin B cyclosporin D cyclosporin G and a process to generate and purify them, via methods such as crystallizations. This approach allows for a rapid, practical and much more effective access to opened cyclosporin A, cyclosporin B, cyclosporin D or cyclosporin G and can be used to produce cyclic undecapeptides, such as alisporivir. Furthermore, the process according to the present disclosure may also be applied to other cyclosporins that can be opened via the same sequence. It was found that opened cyclosporin salts, such as hydrochloric acid (HCl), fluoroboric acid (HBF$_4$), or hexafluorophosphoric acid (HPF$_6$), can be formed at several stages.

The present invention provides novel crystalline intermediates, such as cylosporine esters, such as acetate, pivaloate, and opened cyclosporin A, cyclosporin B, cyclosporin D or cyclosporin G salts such as the HCl salt, the HBF$_4$ salt, or the HPF$_6$ salt, and processes to generate them.

SUMMARY OF THE INVENTION

A process for preparing a compound of formula 3 or a salt thereof is provided, (3)

wherein R is methyl, ethyl, propyl or phenyl and R' is methyl or ethyl. The method includes the steps of acylation of cyclosporin A, to form acetyl-Cyclosporin A; ring opening of the acetyl-Cyclosporin A; and crystallizing the ring opened acetyl-Cyclosporin A to obtain the compound of formula 3.

A process for preparing a compound of formula 4 or a salt thereof is provided, (4)

wherein R is methyl, ethyl, propyl or phenyl and R' is methyl or ethyl. The method includes the steps of Edman degradation of compound of formula 3; and then crystallizing the compound to obtain the compound of formula 4.

A process for preparing a compound of formula 4 or a salt thereof is provided, (4)

wherein R is methyl, ethyl, propyl or phenyl and R' is methyl or ethyl. The method includes the steps of: acylation of cyclosporin A to form acetyl-Cyclosporin A; ring opening of the acetyl-Cyclosporin A; and crystallizing the ring opened acetyl-Cyclosporin A to obtain the compound of formula 3

(3)

Edman degradation of the compound of formula 3; and then crystallizing the compound to obtain the compound of formula 4 or a salt thereof.

A compound of formula 3 or a salt thereof is provided (3)

wherein R is methyl, ethyl, propyl or phenyl and R' is methyl or ethyl.

A compound of formula 4 or a salt thereof is provided (4)

wherein R is methyl, ethyl, propyl or phenyl and R' is methyl or ethyl.

DETAILED DESCRIPTION OF THE INVENTION

The general process according to the present invention for producing cyclic polypeptides, more specifically, cyclic undecapeptides, such as Alisporivir, is shown in the scheme below; however, this general scheme can also be used to make cyclic polypeptides, more specifically, cyclic undecapeptides, derived from cyclosporine A, B, D, or G.

(1)

ester formation →

(2)

ring opening →

-continued crystallization →

(3)

Edman degradation → crystallization →

(4)

wherein R² is:
ethyl for Cyclosporin A
methyl for Cyclosporin B
propyl for Cyclosporin G
isopropyl for Cyclosporin D

Specifically, alisporivir can be made by converting cyclosporin A (compound (1) wherein R² is ethyl) into a compound of formula 4 as shown above by acylation of cyclosporin A, to form acetyl-Cyclosporin A (2); ring opening; crystallization to obtain a compound 3, Edman degradation of compound 3; crystallization to obtain a compound 4 and then cyclizing compound 4 to form alisporivir (as shown below).

(4)

-continued

ALISPORIVIR

The invention specially relates to the processes described in each section. The invention likewise relates, independently, to every single step described in a process sequence within the corresponding section. Therefore, each and every single step of any process, consisting of a sequence of steps, described herein is itself a preferred embodiment of the present invention. Thus, the invention also relates to those embodiments of the process, according to which a compound obtainable as an intermediate in any step of the process is used as a starting material.

The invention also relates to intermediates which have been specifically developed for the preparation of the compounds according to the invention, to their use and to processes for their preparation.

It is noted that in the present application, explanations made in one section may also be applicable for other sections, unless otherwise stated.

Cyclosporin A, cyclosporin B, cyclosporin D or cyclosporin G or salts thereof, may be prepared, for example by fermentation.

In one embodiment the present invention relates to a method for preparing compound of formula 3, comprising the steps of acylation of cyclosporin A, cyclosporin B, cyclosporin D or cyclosporin G to form acetyl-Cyclosporin A, B, D, or G; ring opening; and crystallization.

In one embodiment the present invention relates to a method for preparing compound of formula 4 or a salt thereof, comprising Edman degradation, a reaction well known in the art, of a compound of formula 3 and crystallization thereof to obtain compound of formula 4.

Another embodiment of the present invention relates to a method for preparing a compound of formula 3 or formula 4 wherein the purity of the Cyclosporin A starting material is >80% by weight Another embodiment of the present invention relates to a method for preparing a compound of formula 3 or formula 4 wherein the purity of the Cyclosporin A starting material is >85% by weight.

Another embodiment of the present invention relates to a method for preparing a compound of formula 3 or formula 4 wherein the purity of the Cyclosporin A starting material is 60 to 80%, weight % assay.

In the processes shown above, novel and inventive compounds are involved. Consequently, further subjects of the present invention are the compounds shown below.

Compounds of formula 3 or salts thereof, (3)

wherein R is methyl, ethyl, propyl or phenyl, R' is methyl or ethyl, and $R_2$ is methyl, ethyl, or propyl.

Compounds of formula 4 or salts thereof, (4)

wherein R is methyl, ethyl, propyl or phenyl, R' is methyl or ethyl, and $R^2$ is methyl, ethyl, or propyl.

Compounds of formula 3 or salts thereof, (3)

wherein R is methyl, ethyl, propyl or phenyl and R' is methyl or ethyl.

Compounds of formula 4 or salts thereof, (4)

wherein R is methyl, ethyl, propyl or phenyl and R' is methyl or ethyl.

The following Examples represent preferred embodiments of the reaction steps, intermediates and/or the process of the present invention and serve to illustrate the invention without limiting the scope thereof.

Preparation of Compound 3 $HBF_4$ Salt with Merwein Salt

Acetyl-Cyclosporin A (100 g as is) was reacted with trimethyloxonium tetrafluoroborate (32 g) at 20-25° C. in dichloromethane (180 mL). After 20 h, acetonitrile (200 mL) and water (650 mL) were added to perform the hydrolysis. After 3 h, at 20-25° C., the phases were separated and the reaction mixture was dried by azeotropic distillation with 2-Methyl-Tetrahydrofuran (solvent exchange dichloromethane/2-Methyl-Tetrahydrofuran). The desired product was then crystallized from 2-Methyl-Tetrahydrofuran (900 mL) and 2-Methoxy-2-methylpropane (400 mL) to provide compound 3 $HBF_4$ as a white crystalline powder (63.9 g, after drying, purity >92%). 0.69, (3H,d,J=6.6 Hz); 0.71, (3H,d, J=6.5 Hz); 0.81, (6H,m); [0.82 . . . 0.89], (24H,m); 0.90, (3H,d,J=6.6 Hz); 0.93, (3H,d,J=6.6 Hz); 1.16, (6H,m); [1.23 . . . 1.50], (4H,m); 1.52, (1H,m); [1.32 . . . 1.73], (8H,m); 1.59, (3H,d,J=6.0 Hz); 1.65, (2H,m); 1.65, 2.13, (2H,m); 1.93, 1.94, (3H,s); 2.03, (1H,m); 2.19, (1H,m); 2.45, (3H,s); 2.72, (3H,s); 2.84, (3H,s); 2.86, (3H,s); 2.99, (3H,s); 3.02, (3H,s); 3.06, (3H,s); 3.62, 3.68, (3H,s); 3.78, (1H,m); 3.87, 4.53, (1H,d,J=17.2 Hz,18.6 Hz); 4.10, 4.26, (1H,d, J=18.6 Hz,16.8 Hz); 4.23, (1H,m); 4.60, (1H,m); 4.62, (1H,m); 4.66, (1H,m); 5.02, (1H,m); 5.13, (1H,dd, J=11.3 Hz,4.7 Hz); 5.26, (1H,m); 5.29, (1H,m); 5.32, (1H,m); 5.36, (1H,m); 5.39, (2H,m); 7.72, (1H,d,J=7.3 Hz); 8.14, (1H,d, J=7.3 Hz); 8.21, 8.35, (1H,d,J=7.3 Hz,8.1 Hz); 8.85, (2H,s, br); 8.96, (1H,d,J=8.4 Hz).

Figure 1:
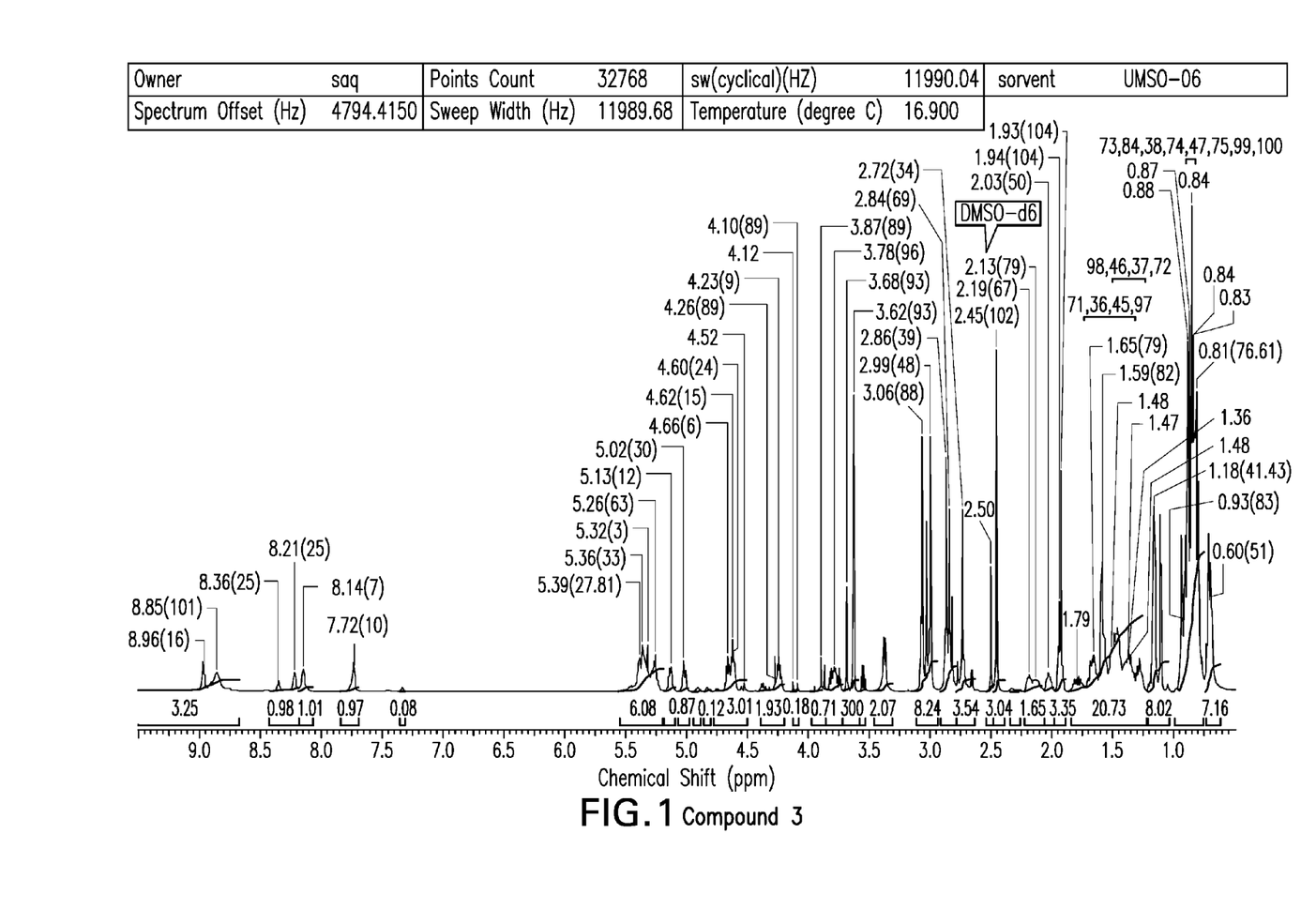
FIG. 1 is a proton NMR spectra for compound 3.

Preparation of Compound 3 $HBF_4$ Salt with Use of Trimethylorthoformate and Borontrifluoride Etherate A solution of Acetyl-Cyclosporin A (10 g) in dichloromethane (20 mL) was added at −15° C. to a slurry of dimethoxycarbenium tetrafluoroborate generate at −20° C. by a slow addition of borontrifluoride (2 ml) to a solution of trimethylorthoformate (2 ml) in dichloromethane (20 mL). After the addition, the slurry was allowed to warm up to room temperature and was kept stirring for 20 h. Afterward, Acetonitrile (10 ml) and water (10 ml) were added. After 2 h stirring at 0° C., phases were split. Then, after having washed the organic phase with water, solvent switched to 2-Methyl-Tetrahydrofuran and saturation with 2-Methoxy-2-methylpropane, compound 3 was obtained as a white solid which was dried under vacuum (5.1 g, >90% purity) (see FIG. 1)

Figure 2:
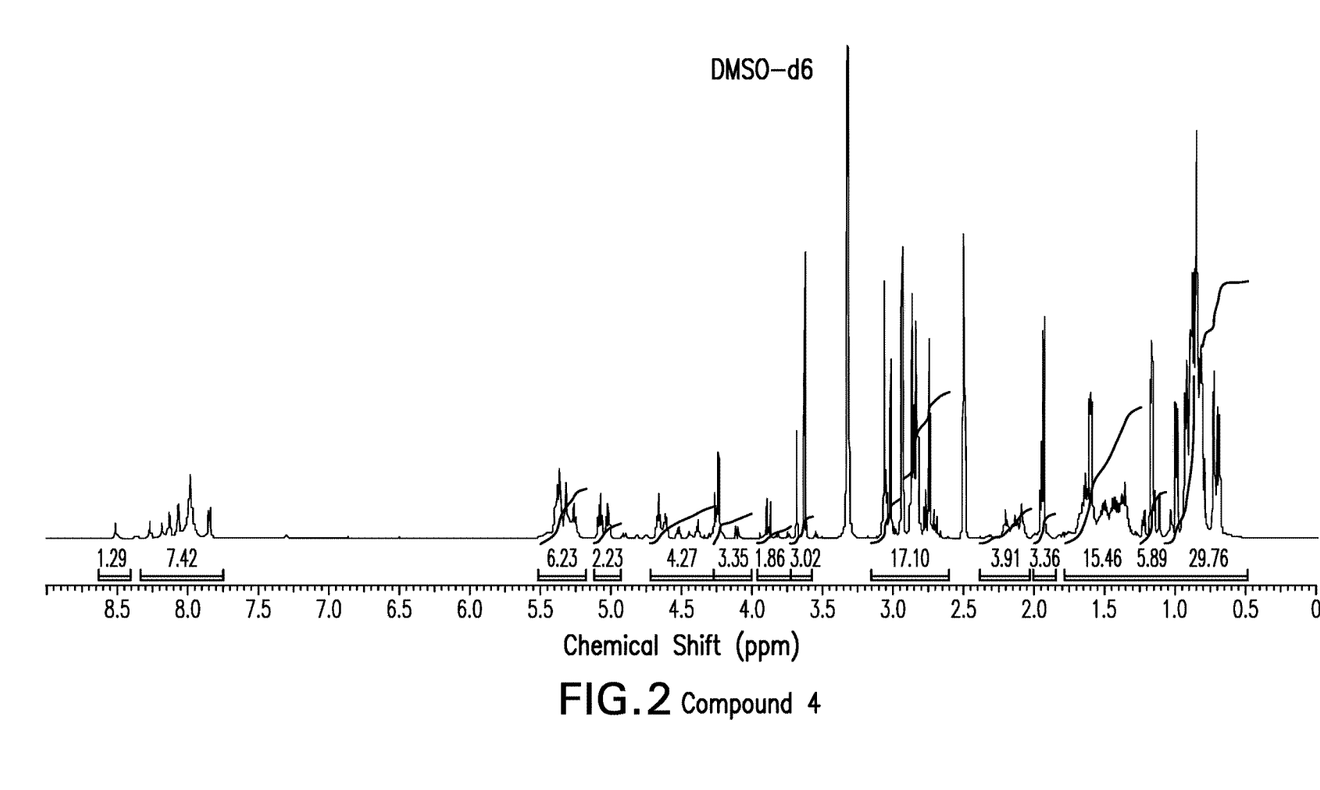
FIG. 2 is a proton NMR spectra for compound 4.

Preparation of Compound $HBF_4$ Salt:

The previously prepared salt of compound 3 (34.62 g) was charged to a reactor along with sodium carbonate (4.8 g), Toluene (50 mL) and water (50 mL). The resulting mixture was stirred at 20-25° C. for 30 minutes, and the phases were separated. Phenylisothiocyanate (3.81 g) was added drop wise in 1 h at 20-25° C. and the resulting reaction mixture was stirred until completion. Then methanol (20 mL), and 48% fluoroboric acid in water (2.5 g) was added and the mixture was stirred for an additional 1 h. Then water (25 mL) was added, and the phases were split. The aqueous layers were extracted once more with toluene (50 mL) and then extracted with 2-Methyl-Tetrahydrofuran (100 mL). The organic extract was dried azeotropically and the desired product was crystallized from 2-Methyl-Tetrahydrofuran (100 mL) and 2-Methoxy-2-methylpropane (50 mL) to provide compound 4 $HBF_4$ as a white crystalline powder (ca. 30 g, after drying, >93% purity). (see FIG. 2) 0.69, (3H,d, J=6.2 Hz); 0.73, (3H,d,J=7.0 Hz); 0.81, (3H,t,J=7.3 Hz,7.3 Hz); 0.82, (3H,m); 0.85, (9H,m); 0.88, (6H,m); 0.91, (3H, d,J=7.0 Hz); 0.93, (3H,d,J=6.6 Hz); 0.99, (3H,d,J=7.0 Hz); 1.17, (6H,d,J=6.6 Hz); [1.30 . . . 1.55], (9H,m); 1.60, (3H,d,J=5.5 Hz); [1.56 . . . 1.72], (4H,m); 1.93, 1.95 (3H,s); 2.09, (1H,m); 2.14, (1H,m); 2.20, (1H,m); 2.74, (3H,s); 2.82, 3.06, (3H,s); 2.84, (3H,s); 2.87, (3H,s); 2.94, (3H,s); 3.02, (3H,s); 3.63, 3.68, (3H,s); 3.88, 4.52, (1H,d,J=17.2 Hz,18.6 Hz); 4.10, 4.24, (1H,d,J=18.7 Hz,m); 4.24, (2H,m); 4.39, 4.62, (1H,m); 4.66, (1H,m); 5.02, (1H,m); 5.08, (1H,m); 5.26, (2H,m); 5.32, (1H,m); 5.37, (1H,m); 5.39, (2H,m); 7.84, 8.51 (1H,d,J=7.3 Hz,8.1 Hz); 7.98, (3H,s,br); 8.07, 8.18 (1H,d,J=7.7 Hz,7.3 Hz); 8.13, 8.27, (1H,d,J=7.3 Hz,8.1 Hz).

Preparation of Alisporivir:

The previously described intermediate 4 (ca. 109 g) was added in portions at 15° C. to a mixture of toluene and sodium carbonate/water and stirred for 3 hours at 15° C. The aqueous phase was separated. The dipeptide (ca. 28 g) and

N-hydroxybenzotriazole-mono-hydrate (8.1 g) was added at 0° C. Water (2.5 mL) was added to the mixture and N-methylmorpholine (17.9 g) was dosed at −10° C., followed by a solution of dicyclohexylcarbodiimide (21.9 g) in toluene dosed at −10° C. and stirred at that temperature for 3 hours. The reaction mixture was heated to 0° C. in a period of 10 hours. At completion, the reaction mixture was filtered and the filtrate was extracted with 5% sodium carbonate solution, 5% salt solution, 2M hydrochloric acid and 10% salt solution. The organic phase was filtered again and concentrated at 50° C. in vacuum.

Sodium Borohydride (0.59 g) was dissolved in diglyme (14.3 g) at 20 to 40° C. The cloudy solution was chilled to 12-16° C. Glycine (0.59 g) was added at that temperature. The previously prepared product (6.2 g) in solution into ca. 6 g toluene was dosed to the white suspension at 12-16° C. Then the reduction was accelerated by adding methanol in toluene at 12-16° C. This addition was controlled and performed in 3 portions. The reaction was stirred for an additional 3 hours, and added to the quench solution (aqueous acetic acid) at an internal temperature of 10-20° C. The rate of addition was modified in line with the hydrogen evolution (no accumulation). The phases were separated, the upper organic product phase was extracted with water and subsequently concentrated.

The previously prepared product (5 g) was dissolved in toluene (ca. 5 g) and dosed in a period of 40-60 minutes to a solution of sulphuric acid (0.8 g) in methanol (50 mL) at 50° C. After ca. 2 hours, the solution was chilled to 15-20° C. and 25% benzyltrimethylammoniumhydroxide (ca. 12 g) in methanol was dosed (exothermic reaction). After 2 hours, water was dosed and the mixture was stirred for approx. 20 hours at 22° C. At completion, the solution was chilled to 10-15° C., diluted with water and neutralised with dilute sulphuric acid. Following separation of the top toluene phase, methanol was removed from the lower product phase by distillation. The oily separated product was extracted with ethyl acetate and washed in sequence with water and salt solution, adjusting the pH to 7.0-7.5 with dilute sulphuric acid. Then the organic phase was dried azeotropically and then precipitated onto 0-5° C. cold heptane. The product suspension was filtered, washed with heptane and dried in vacuum at 60° C.

The "undecapeptide amino acid" precursor (5 to 13% to the overall end mass) dissolved in dichloromethane and the DCC dissolved into dichloromethane were added continuously in parallel in ca. 10 h to a mixture of Cl-HOBT, and NMM in dichloromethane at 40° C. At the end of the addition, the mixture was stirred for an additional 2 h, filtered to remove the DCU salt and concentrated to give Alisporivir as a crude product.

The invention claimed is:
1. An HBF$_4$ salt of

2. An HBF4 salt of

* * * * *